(12) United States Patent
Chen

(10) Patent No.: US 7,405,083 B2
(45) Date of Patent: Jul. 29, 2008

(54) METHOD AND APPARATUS FOR PURIFYING AND DESALTING BIOLOGICAL SAMPLES

(75) Inventor: Xiaoxi (Kevin) Chen, Waltham, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 504 days.

(21) Appl. No.: 10/844,777

(22) Filed: May 13, 2004

(65) Prior Publication Data

US 2004/0226885 A1 Nov. 18, 2004

Related U.S. Application Data

(60) Provisional application No. 60/469,986, filed on May 13, 2003, provisional application No. 60/470,021, filed on May 13, 2003, provisional application No. 60/538,913, filed on Jan. 23, 2004, provisional application No. 60/564,927, filed on Apr. 23, 2004.

(51) Int. Cl.
*G01N 1/18* (2006.01)
*G01N 1/00* (2006.01)
*G01N 30/02* (2006.01)
*B01L 11/00* (2006.01)

(52) U.S. Cl. ............... 436/178; 436/174; 436/175; 436/176; 436/177; 422/70; 422/101

(58) Field of Classification Search ......... 436/174–178; 422/70, 101
See application file for complete search history.

(56) References Cited

U.S. PATENT DOCUMENTS

| | | |
|---|---|---|
| 3,111,489 A | 11/1963 | Getzin |
| 3,540,856 A | 11/1970 | Rochte et al. |
| 3,540,857 A | 11/1970 | Martin |
| 3,540,858 A | 11/1970 | Rochte et al. |
| 4,304,865 A | 12/1981 | O'Brien et al. |
| 4,789,601 A | 12/1988 | Banes |

(Continued)

FOREIGN PATENT DOCUMENTS

EP  1 139 087 A2  10/2001

(Continued)

OTHER PUBLICATIONS

Chen, Xiaoxi et al., "A Prototype Two-Dimensional Capillary Electrophoresis System Fabricated in Poly(dimethylsiloxane)", Analytical Chemistry vol. 74 pp. 1772-1778, 2002.

(Continued)

*Primary Examiner*—Jill Warden
*Assistant Examiner*—Keri A Moss
(74) *Attorney, Agent, or Firm*—Nanette S. Thomas

(57) ABSTRACT

The subject invention provides a sample processing technique for purifying a biological or chemical sample. The invention is particularly well-suited to prepare a sample for mass spectrometry. The process is to be performed in an article having at least one well, in which the surface of the well is at least partially hydrophobic and/or modified with bio-specific ligands. Targeted solutes, such as salts or small molecule contaminants, can be removed from a solution to allow for a purified solution of a desired type of solute, such as peptides and/or proteins.

25 Claims, 21 Drawing Sheets

U.S. PATENT DOCUMENTS

| | | |
|---|---|---|
| 4,948,442 A | 8/1990 | Manns |
| 5,047,215 A | 9/1991 | Manns |
| 6,074,827 A | 6/2000 | Nelson et al. |
| 6,309,605 B1 | 10/2001 | Zermani |
| 6,485,690 B1 | 11/2002 | Pfost et al. |
| 2001/0001644 A1 | 5/2001 | Coffman et al. |
| 2002/0034827 A1 | 3/2002 | Singh et al. |
| 2003/0017079 A1* | 1/2003 | Hahn et al. .............. 422/82.09 |
| 2004/0126890 A1* | 7/2004 | Gjerde et al. ................. 436/53 |

FOREIGN PATENT DOCUMENTS

| | | |
|---|---|---|
| WO | WO 01/19520 A1 | 3/2001 |
| WO | WO 03/012392 A2 | 2/2003 |

OTHER PUBLICATIONS

McDonald, et al., "Fabrication of microfluidic systems in poly(dimethylsiloxane)", Electrophoresis 2000, 21, pp. 27-40.
European Search Report dated Dec. 27, 2004 from European Application No. 04102107.2.

* cited by examiner

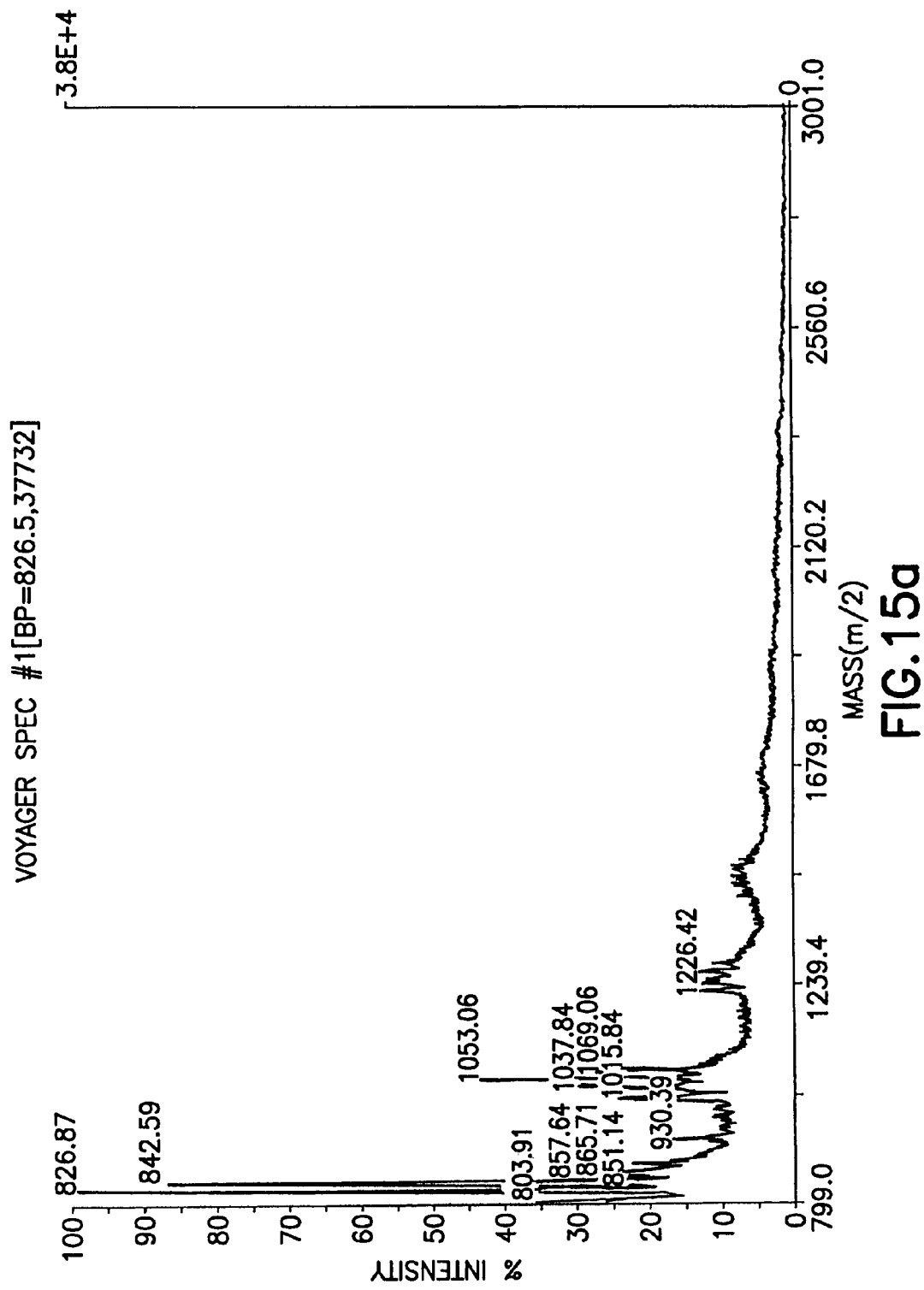

METHOD AND APPARATUS FOR PURIFYING AND DESALTING BIOLOGICAL SAMPLES

CROSS-REFERENCES TO RELATED APPLICATIONS

This application claims priority of U.S. Provisional Patent Application No. 60/469,986, filed May 13, 2003; U.S. Provisional Patent Application No. 60/470,021, filed May 13, 2003; U.S. Provisional Patent Application No. 60/538,913, filed Jan. 23, 2004; and U.S. Provisional Patent Application No. 60/564,927, filed Apr. 23, 2004, all of which are hereby incorporated by reference.

FIELD OF INVENTION

This invention relates to methods and apparatuses for processing biological and chemical samples.

BACKGROUND OF THE INVENTION

Conventional techniques exist for conducting mass spectrometric analysis of large molecules using MALDI (matrix-assisted laser desorption and ionization) plates. Typically with these techniques, liquid solutions (including e.g., peptide, protein, and energy absorbing matrix) are initially introduced to pre-defined target sites on a MALDI plate. Since the diameter of the target sites are generally small and often densely packed, small (e.g., 1-5 microliter) droplets of the liquid solutions are disposed onto the plate target sites to achieve proper sample placement and to avoid sample overlap between target sites. Once disposed, the liquid samples are evaporated, with matrix crystal conglomerate containing analyte molecules (e.g., peptides and proteins) remaining on the target sites having favorable characteristics for the MALDI process and mass spectrometric analysis. Where larger conglomerate samples are desired, serial liquid sample placement and evaporation has been used to iteratively build-up a conglomerate.

Prior to placement on the MALDI plate, the liquid solution is typically purified and desalted. Such purification and desalting is achieved in the prior art with columns, pipette tips or multi-well filter plates being packed with C18 media or other chromatography media. Examples of columns packed with C18 media include Pierce PepClean™ C18 Spin Columns and 3M Empore™ Extraction Disk Cartridge. Examples of pipette tips packed with C18 media include Millipore ZipTip® Pipette Tips and Varian OMIX Pipette Tips C18. Examples of multi-well filter plates packed with C18 media include Millipore Zip Plate Micro-SPE Plate and 3M Empore™ 96-Well Extraction Disk and Plate.

For exemplary purposes, a common procedure for purifying and desalting liquid solution samples using one of the above-identified devices includes initially wetting the C18 media with a buffer containing an organic solvent, such as methanol or acetonitrile, and thereafter, equilibrating the C18 media with an equilibration buffer. The liquid solution samples are then flowed through the C18 media; it is expected that peptides and proteins of the sample be retained in the C18 media during this step. Thereafter, the C18 media is washed with a washing buffer, and, again, the peptides and proteins are expected to be retained in the media during this step. Finally, a flow elution buffer is passed through the C18 media which disassociates the peptides and proteins from the media, and it is expected that the peptides and proteins flow out with the elution buffer in this step.

A significant portion of the peptides and proteins in the sample solution may flow through the C18 media or other chromatography media in the prior art devices without binding to the C18 or other media. As a result, recovery of the peptides and proteins may be poor, particularly where the sample concentration is low.

SUMMARY OF THE INVENTION

The subject invention provides a sample processing technique for purifying a biological or chemical sample. The invention is particularly well-suited to prepare a sample for mass spectrometry, such as preparing a sample for use with a MALDI plate. The process is to be performed in an article having at least one well, in which the surface of the well is at least partially hydrophobic and/or modified with bio-specific ligands. With the process of the subject invention, a sample solution is added to the well, with the solution including two types of solutes: a first type of solutes (such as peptides and proteins) which are able to bind tightly to the well surface through hydrophobic interactions or through interactions with the bio-specific ligands immobilized on the well surface, and a second type of solutes (such as salts or small molecule contaminants) which are not able to bind tightly to the well surface. Once added, the sample solution is dried in the well, leaving all of the solutes deposited on the well surface. A buffer, which is not able to disassociate the first type of solutes from the well surface but is able to disassociate the second type of solutes from the well surface, is added to the well. Consequently, the second type of solutes is dissolved into the first buffer, while the first type of solutes remains bound to the well surface. The first buffer, now containing the second type of solutes, is removed from the well, leaving the first type of solutes bound to the well surface. The first buffer can be serially added and removed to maximally remove the second type of solutes. Thereafter, a second buffer, which is able to disassociate the first type of solutes from the well surface, is added to the well. The first type of solutes is dissolved into the second buffer, thus, providing a purified solution of the first type of solutes. Optionally, the second buffer may be allowed to evaporate, thereby, increasing its concentration.

The process of the subject invention can be practiced in a column, pipette or multi-well plate, with the purified solution being later applied to a target plate or other desired analysis device. Additionally, the process of the subject invention can be practiced with a target support plate which can be releaseably secured to a target device, such as a MALDI plate. With a target support plate, the liquid sample can be purified in the target support plate and on the device, and, then, evaporated to allow a conglomerate to be directly formed on the target plate with no transference of the liquid sample being required.

These and other features of the invention will be better understood through a study of the following detailed description and accompanying drawings.

BRIEF DESCRIPTION OF THE DRAWINGS

FIGS. 4-7 shows various target support plate and target device assemblies, wherein FIG. 5 is an enlarged view of Section 5 in FIG. 4.

DETAILED DESCRIPTION OF THE INVENTION

Provided herein is a new process for purifying a biological or chemical sample. The process is particularly well-suited for preparing liquid samples for mass spectrometry, such as preparing a sample for use with a MALDI plate. As will be described below, the process can be practiced remotely from the device intended to analyze the sample or practiced in contiguous contact therewith.

Figure 1:
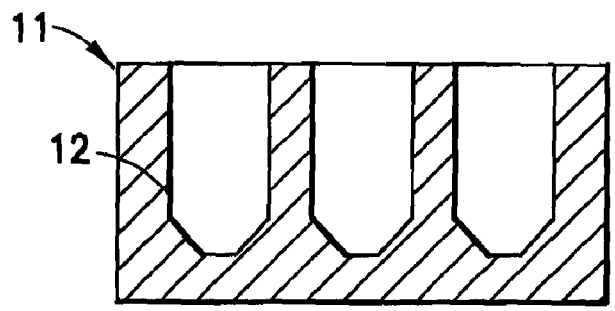
FIGS. 1, 1(*b*) and 1(*c*) are schematics, of a multi-well plates, a column, and a pipette usable with the subject invention.
Figure 1B:
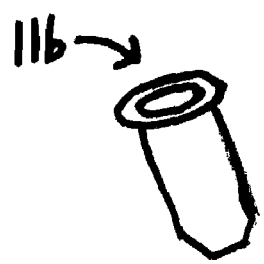
Figure 1C:
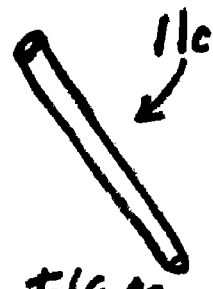

With reference to FIGS. 1 and 2(a)-(f), a multi-well plate 11 is shown having one or more wells 12 defined therein as is known in the art. At least one of the wells 12 is formed with a surface that is hydrophobic and/or modified with bio-specific ligands (such as immobilized metal ion affinity chromatography (IMAC) matrices for phosphorylated peptides/proteins or poly(histidine) fused peptides/proteins, biotin affinity matrices for biotinylated peptide/proteins, and thiol-disulfide exchange chromatography matrices for glutathione S-transferase (GST) fused peptides/proteins). It is to be understood that the process of the subject invention can be practiced with structures other than a multi-well plate, including, but not limited to, a target support plate (as described below), a column 11b (FIG. 1(b)) and a pipette 11c (FIG. 1(c)). With any structure, it is desired that a well be provided within the device in which a surface that comes into contact with the liquid sample be hydrophobic and/or modified with bio-specific ligands. The entire well surface need not be hydrophobic and/or modified with bio-specific ligands. The well surface can be inherently hydrophobic or treated to be hydrophobic (e.g., by coating with alkyl silanes or hydrophobic polymers).

Figure 2A:
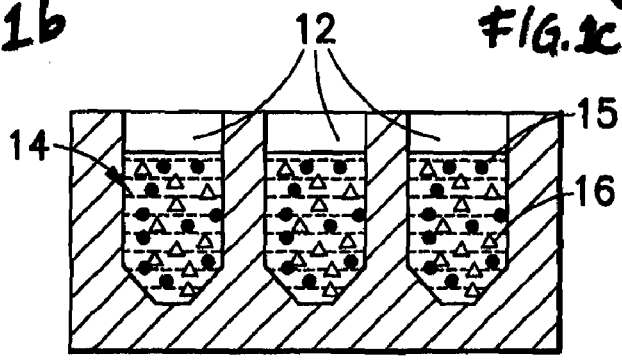
FIGS. 2(*a*)-(*f*) show the process of the subject invention being practiced in a multi-well plate.

As shown in FIGS. 2(a)-(f), the subject invention includes sequential steps for purifying a liquid sample. The liquid sample may be a known liquid sample used in preparing analytes for the MALDI process or other mass spectrometric processes (such as liquid samples which contain tryptic digest products). Specifically, the process seeks to eliminate salts and other contaminants from a sample solution, while maintaining peptides and proteins therein at the highest possible level. With reference to FIG. 2(a), a liquid sample solution 14 is introduced into one or more wells 12. The solution 14 contains two types of solutes designated with the reference numerals 15 and 16 (the black solid circles represent the first type of solutes 15 while the open triangles represent the second type of solutes 16). The first type of solutes 15 are able to bind tightly to the surfaces of the wells 12 through hydrophobic interactions or through interactions with the bio-specific ligands immobilized on the well surfaces. The first type of solutes 15 may include peptides and proteins. It should be noted that when peptides and proteins are in proximity to a hydrophobic surface in aqueous solutions, they will be adsorbed to the hydrophobic surface. The second type of solutes 16 are not able to bind tightly to the well surfaces and may be salts or small molecule contaminants.

Figure 2B:
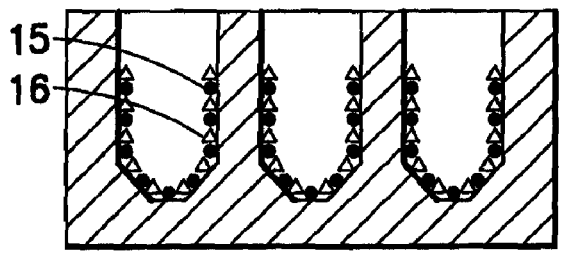
Figure 2C:
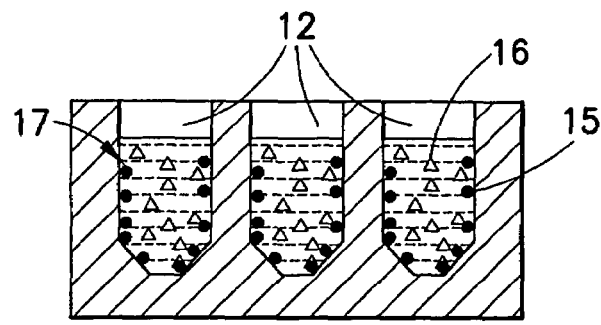
Figure 2D:
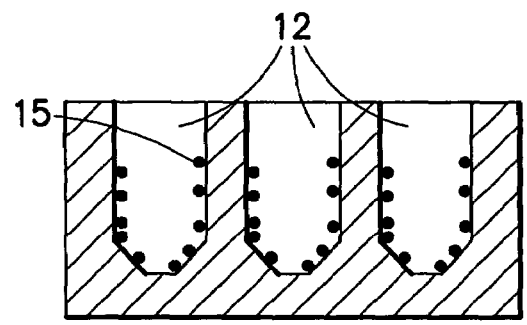
Figure 2E:
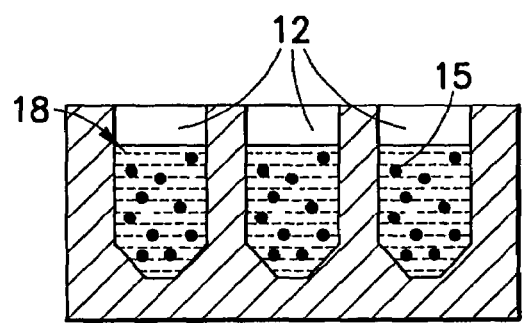
Figure 2F:
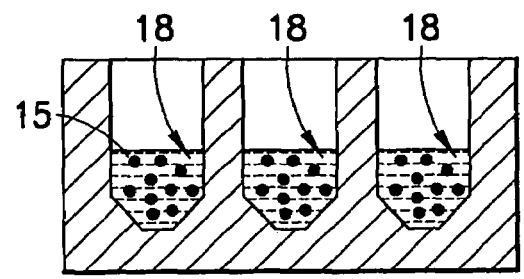

Once the solution is deposited, the solution 14 is evaporated or dried off leaving the solutes 15 and 16 deposited on the well surfaces, as shown in FIG. 2(b). Thereafter, a first buffer 17, which is not able to disassociate the first type of solutes 15 from the well surfaces but is able to disassociate the second type of solutes 16 from the well surfaces, is added to the wells 12 (FIG. 2(c)). The first buffer 17 preferably is primarily formed of water. As shown in FIG. 2(c), the second type of solutes 16 dissolve in the first buffer 17, while the first type of solutes 15 remain bound to the well surfaces. With reference to FIG. 2(d), the first buffer 17, containing the second type of solutes 16, is removed from the wells 12, leaving the first type of solutes 15 bound to the well surfaces. The first buffer 17 can be serially added and removed to maximally remove the second type of solutes 16. Thereafter, a second buffer 18 is added to the wells 12. The second buffer 18 is able to disassociate the first type of solutes 15 from the well surfaces. Preferably, the second buffer 18 contains an organic solvent such as acetonitrile or methanol, and, more preferably, is primarily acetonitrile. Additionally, the second buffer 18 may include an energy absorbing matrix such as α-cyano-4-hydroxy cinnamic acid, 3,5-dimethoxy-4-hydroxy cinnamic acid, or 2,5-dihydroxybenzoic acid. With the second buffer 18, the first type of solutes 15 are dissolved into the second buffer 18 providing a purified solution of the first type of solutes 15 (FIG. 2(e)). Optionally, and as shown in FIG. 2(f), a higher concentration of the first type of solutes 15 can be obtained by allowing the second buffer 18 to evaporate.

Figure 3A:
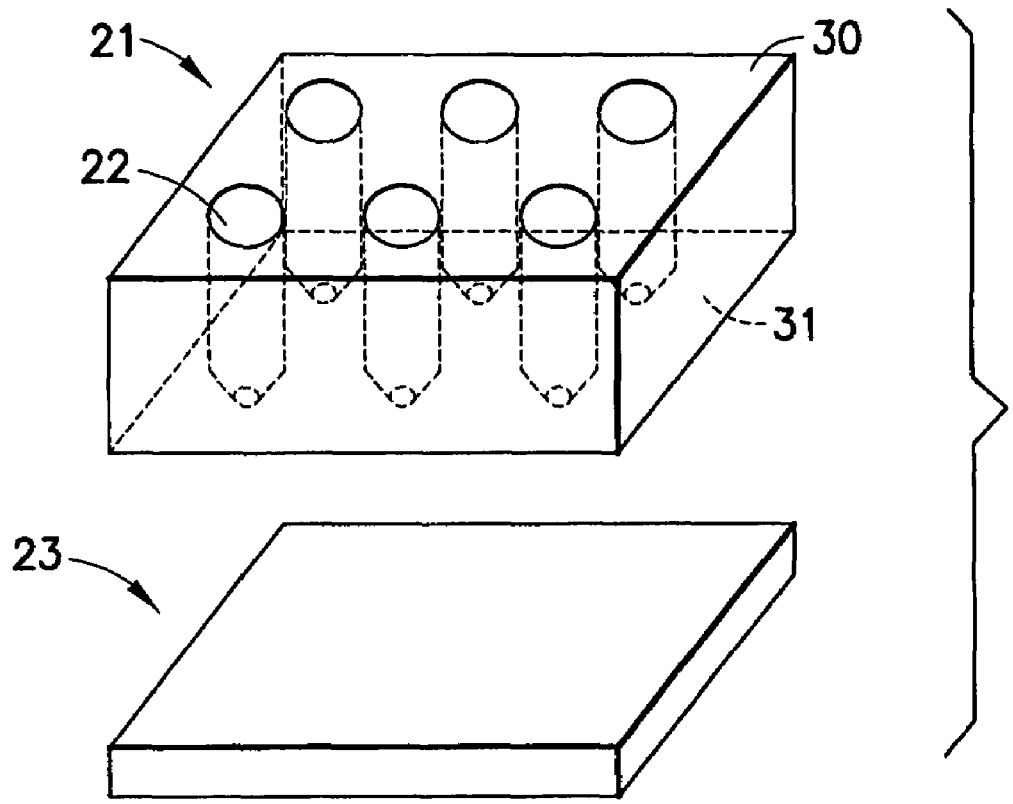
FIGS. 3(*a*) and (*b*) schematically show a target support plate and target device usable with the subject invention.
Figure 3B:
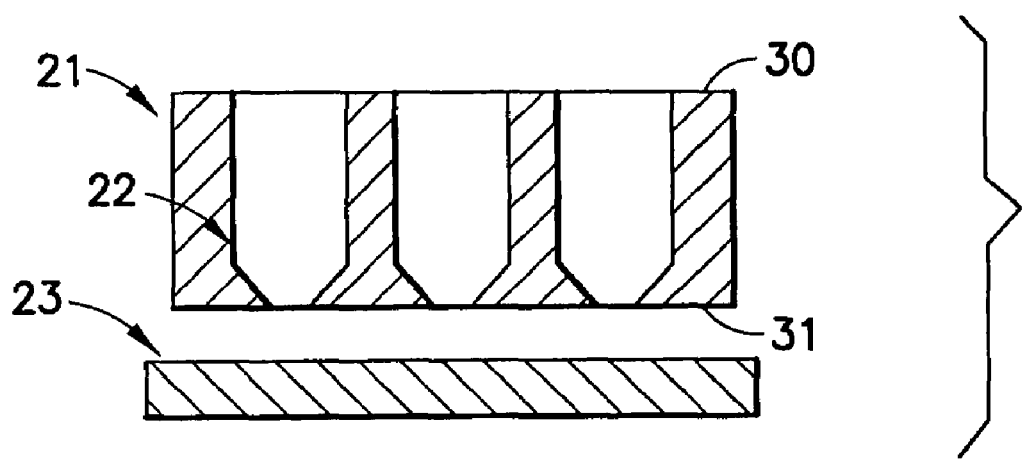

As described above, the subject application can be used with various devices which define one or more of the wells 12. The wells 12 may be defined wholly by one component (e.g., a multi-well plate) or by a combination of two or more components, such as with a target support plate secured to a target device. With reference to FIGS. 3(a)-(b), a target support plate 21 is shown having one or more columns 22 extending between, and through, top and bottom surfaces 30 and 31. The target support plate 21 is releasably securable to a target device 23, such as a MALDI plate or other mass spectrometry plate having one or more collection sites (e.g., a SELDI (Surface Enhanced Laser Desorption/Ionization) plate, or a DIOS (Desorption/Ionization on Porous Silicon) plate). The columns 22 and the target device 23 collectively define fluid-containing wells. Preferably, the target support plate 21 is formed of an elastomeric material which can be releasably secured to the target device 23. It is preferred that the elastomeric material include a silicon polymer, and more preferably, include poly(dimethyl)siloxane (PDMS). With an elastomeric material, van der Waals interactions between the surface molecules of the target support plate 21 and the target device 23 provide for a releasable securement. The target support plate 21 can be pressed onto the target device 23 for securement and removed therefrom by peeling. It is further preferred that the body of the target support plate 21 be wholly formed of the elastomeric material, more preferably being wholly formed of PDMS. The elastomeric and hydrophobic natures of PDMS allow for a tight bond to be formed between the target support plate 21 and the target device 23. With the target support plate 21 being only partially formed of the elastomeric material, remaining portions may be formed of rigid plastic or other material which will impart favorable characteristics to the walls of the columns 22. The securement is preferably of sufficient integrity to prevent cross-contamination between the columns 22 along the target support plate 21/target device 23 interface. Optionally, the walls of the columns 22 may be modified with bio-specific ligands.

Figure 4:
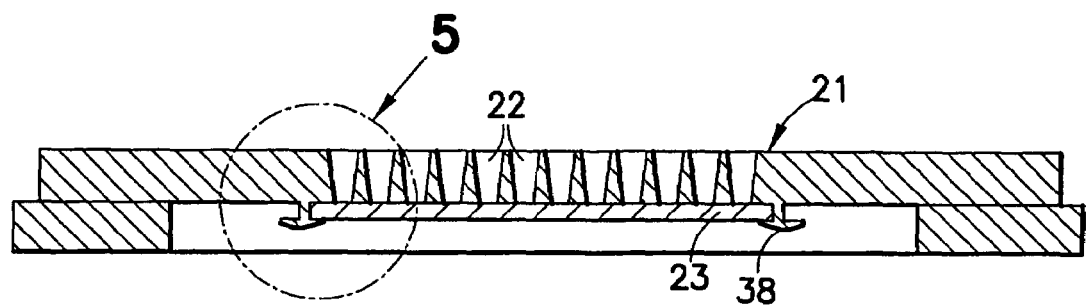
Figure 5:
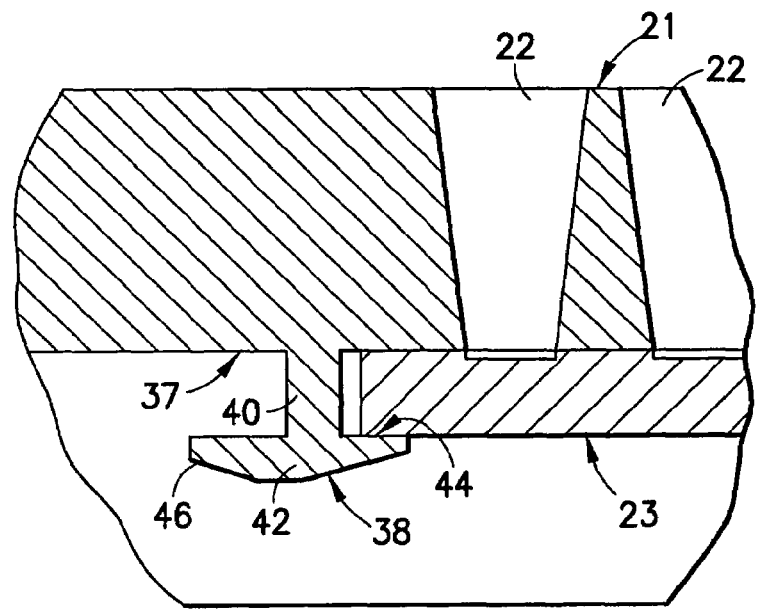

Other forms of the target support plate 21 may be used which allow for releasable securement with the target device 23. The target support plate 21 may rely on adhesive, an elastomeric gasket, and/or a releasable mechanical fixation to allow for releasable securement between the target support plate 21 and a target device 23. With reference to FIGS. 4 and 5, a mechanical fixation is disclosed, wherein a mechanical locking member 38 may be provided which protrudes from the bottom surface 37 to at least partially bound the target device 23. The locking member 38 includes an upstanding support member 40 and a transverse member 42. The upstanding support member 40 and the transverse member 42 are formed such that a portion of the target device 23 is interposed between an engagement surface 44, defined on the transverse member 42, and the bottom surface 37. The transverse member 42 may also include a rearwardly, extending protruding member 46. The target device 23 can be "snapped" into releasable securement with the locking member 38 deflecting and returning to the position shown in FIGS. 4 and 5. Removal of the target device can be achieved by rearward displacement of the protruding member 46 resulting in moment being applied about the upstanding support member 40, deflection of the locking member 38, and separation of the engagement surface 44 from the target device 23. As can be appreciated, the strength of the holding force applied to the target device 23, as well as the difficulty of securement and removal of the target device 23, will be a function of the strength of the locking member 38, and the extent to which the locking member 38 bounds the target device 23.

Figure 6:
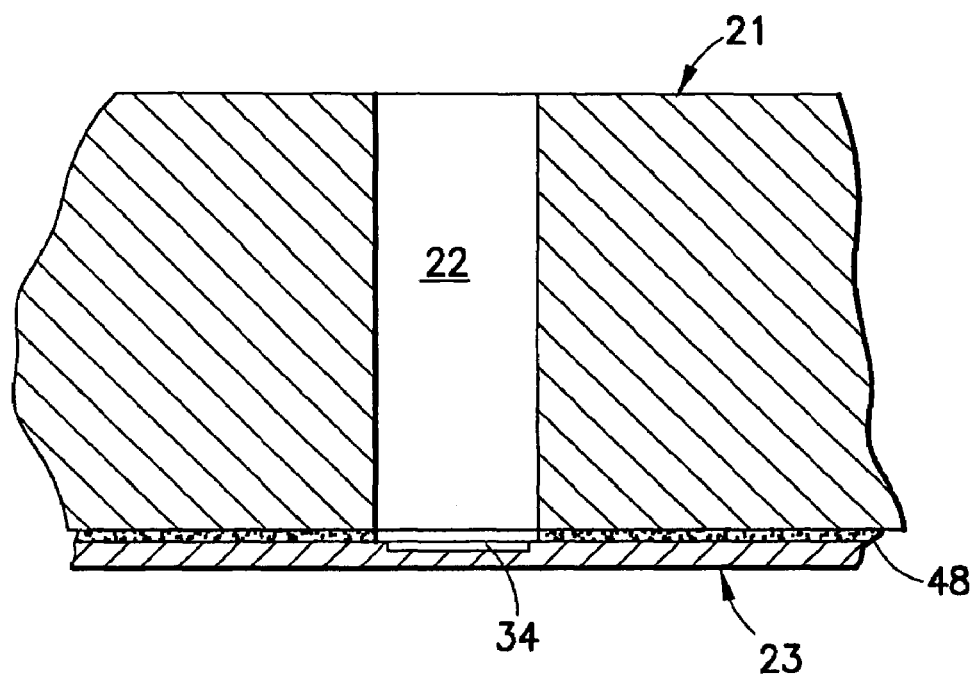

As shown in FIG. 6, adhesive 48 may be used to releasably secure the target device 23 to the target support plate 21. Any suitable adhesive may be used which will allow for release of the target support plate 21, yet provide sufficient holding force to the target support plate 21 to allow for preparation of collection sites 34.

Figure 7:
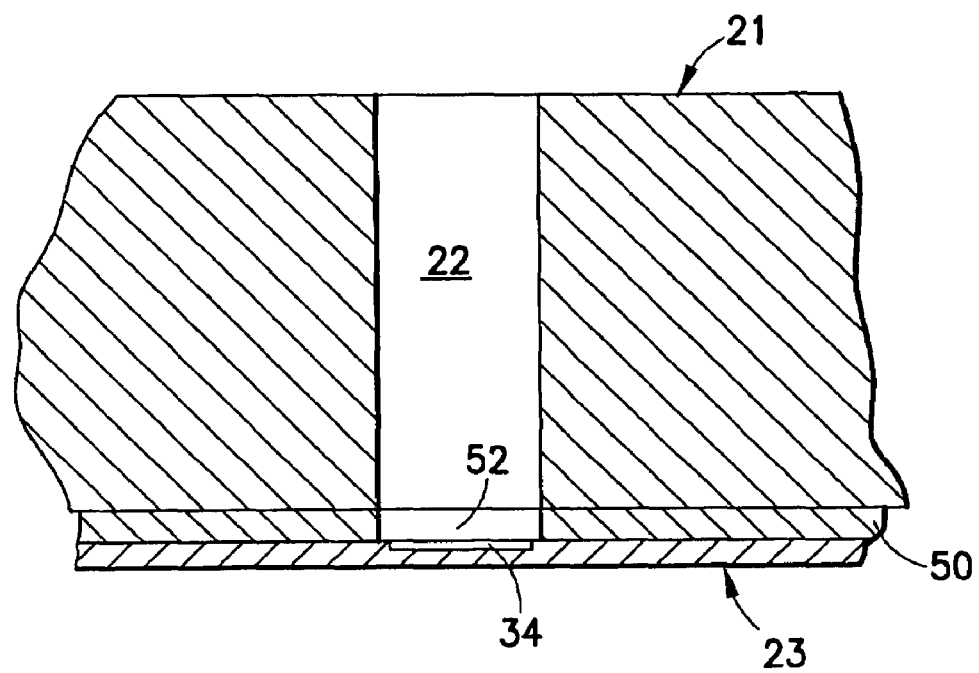
Figure 8A:
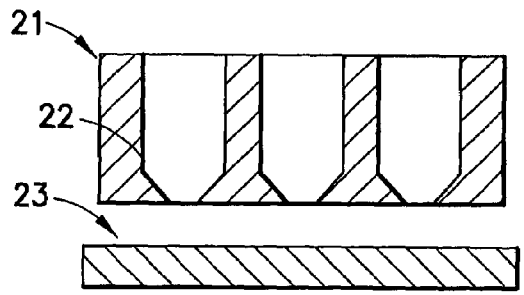
FIGS. 8(a)-(j) show the process of the subject invention being practiced with a target support plate and target device.
Figure 8B:
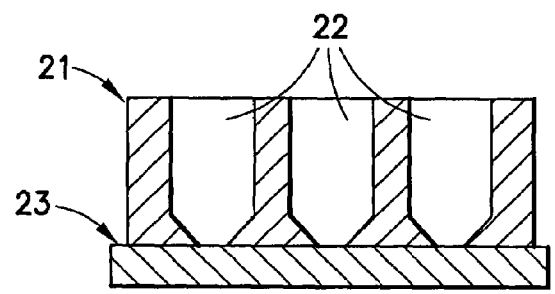
Figure 8C:
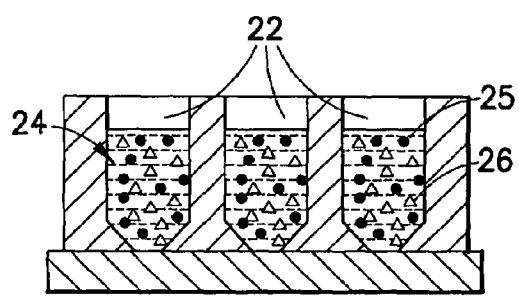
Figure 8D:
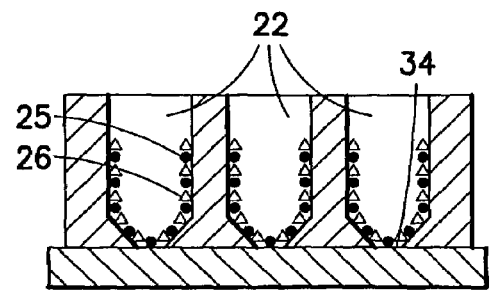
Figure 8E:
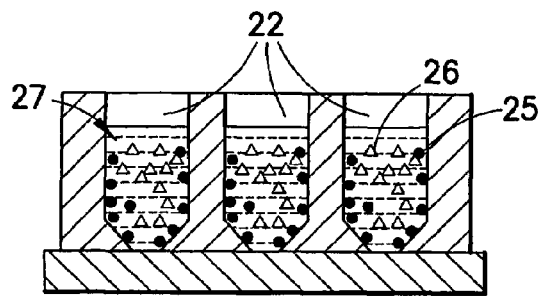
Figure 8F:
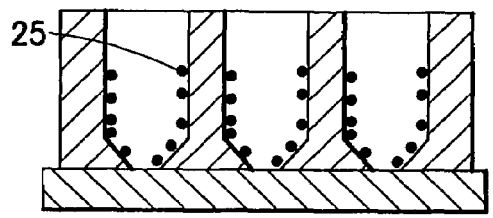
Figure 8G:
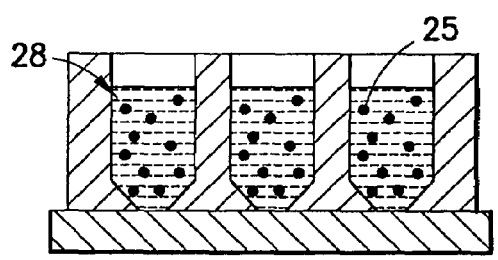
Figure 8H:
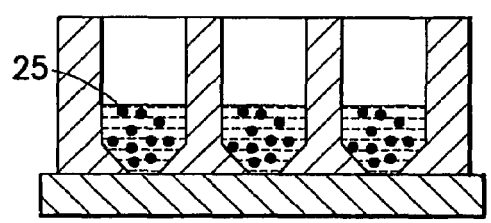
Figure 8I:
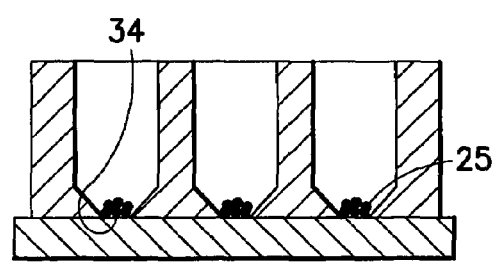
Figure 8J:
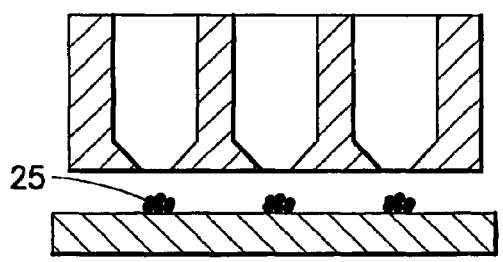

As shown in FIG. 7, an elastomeric gasket 50 may be interposed between the target device 23 and the target support plate 21 to provide releasable securement therebetween. In the same manner as described above with the body of the target support plate 21 being formed of an elastomeric material, the elastomeric gasket 50 provides releasable adhesion. This adhesion may be achieved by van der Waals interactions. Preferably, the elastomeric material of the gasket 50 includes silicon polymer, and more preferably, includes poly(dimethyl)siloxane (PDMS). The elastomeric material may also be doped with other polymers to customize its physical properties. It is further preferred that the elastomeric gasket 50 be wholly formed of PDMS. Apertures 52 shall be formed in the gasket 50 as required to expose the intended collections sites 34. It is preferred that the apertures 52 each have a diameter that is greater than, or equal to, that of the open bottom ends of the columns 22.

As will be understood by those skilled in the art, regardless of the manner by which releasable securement is achieved, it is desired that sufficient sealing be provided along the interface between the target support plate 21 and the target device 23 to prevent cross-contamination of any liquid samples contained in the columns 22. The sealing should be at least fluid-tight. In addition, the level of strength of the releasable securement must be considered in view of any processing steps the assembly is to be subjected to. Adhesive and elastomeric sealing will generally provide a weaker holding force than a mechanical fixation and may be used with smaller volume liquid samples and/or lighter target devices; whereas, a mechanical fixation may be used with larger liquid samples and/or heavier target devices. This is particularly so where the assembly is intended to be centrifuged or otherwise transported together with releasable securement being maintained. On the other hand, the target device 23 should be detached without damage thereto. The various forms of releasable securement can be used in varying combinations (for example, adhesive may be used in combination with mechanical fixation).

It is preferred that the target support plate 21 be wholly formed from PDMS. PDMS is inherently hydrophobic, and as such, by wholly forming the target support plate 21 of PDMS, the walls of the columns 22 will be inherently hydrophobic.

With reference to FIGS. 8(*a*)-(*j*), the process of the subject invention is shown in conjunction with the use of the target support plate 21/target device 23 combination. Initially, as shown in FIGS. 8(*a*) and (*b*), the target support plate 21 is secured to the target device 23. Thereafter, a liquid sample solution 24 (such as a solution containing tryptic digest products) is placed into the columns 22 (FIG. 8(*c*)) which includes two types of solutes 25 and 26: the first type of solutes 25 (represented by solid circles) are able to bind tightly to the column surfaces through hydrophobic interactions or through interactions with the bio-specific ligands immobilized on the column surfaces (e.g., peptides and proteins), while the second type of solutes 26 (represented by open triangles) are not able to bind tightly to the column surfaces, e.g., salts or small molecule contaminants. Upon drying or evaporating the sample solution 24 (FIG. 8(*d*)), the solutes 25 and 26 are deposited on the column surfaces and possibly to some extent on the target device 23. Because of adsorptive attraction, the first type of solutes 25 will tend to be deposited on the walls of the columns 22, rather than on the surface or collection site 34 of the target device 23. A first buffer 27 is next added which is not able to disassociate the first type of solutes 25 from the surfaces of the columns 22 but is able to disassociate the second type of solutes 26 from the column surfaces. As a result, the second type of solutes 26 are dissolved into the first buffer 27, while the first type of solutes 25 remain bound to the column surfaces (FIG. 8(*e*)). The first buffer 24, containing the dissolved second type of solutes 26, is removed from the columns 22, leaving the first type of solutes 25 bound to the column surfaces (FIG. 8(*f*)). The steps of adding and removing the first buffer 27 can be repeatedly conducted to maximally remove the second type of solutes 26. Subsequently, a second buffer 28, as shown in FIG. 8(*g*), is added to the columns 22, which is able to disassociate the first type of solutes 25 from the column surfaces. As a result, the first type of solutes 25 is dissolved into the second buffer 28, thereby providing a purified solution of the first type of solutes 25. The second buffer 28 can be evaporated to increase the concentration of the resulting liquid (FIG. 8(*h*)). Complete evaporation of the second buffer 28 results in the deposition of the first type of solutes 25 onto the target device 23 within the areas at the bottom of the respective columns 22 (FIG. 8(*i*)). The deposition sites coincide with the collection sites 34 on the target device 23. For analysis purposes, the target support plate 21 is removed from the target device 23, for example by peeling (FIG. 8(*j*)). The deposited first type of solutes 25 form sample spots which can be used in further analysis, such as with mass spectrometry, e.g., MALDI mass spectrometry analysis.

As with the method described above, the first buffer 27 is preferably primarily of water, and the second buffer 28 contains an organic solvent, such as acetonitrile or methanol, and, more preferably, primarily acetonitrile. Additionally, the second buffer 28 may include an energy absorbing matrix such as α-cyano-4-hydroxy cinnamic acid, 3,5-dimethoxy-4-hydroxy cinnamic acid, or 2,5-dihydroxybenzoic acid.

Figure 9A:
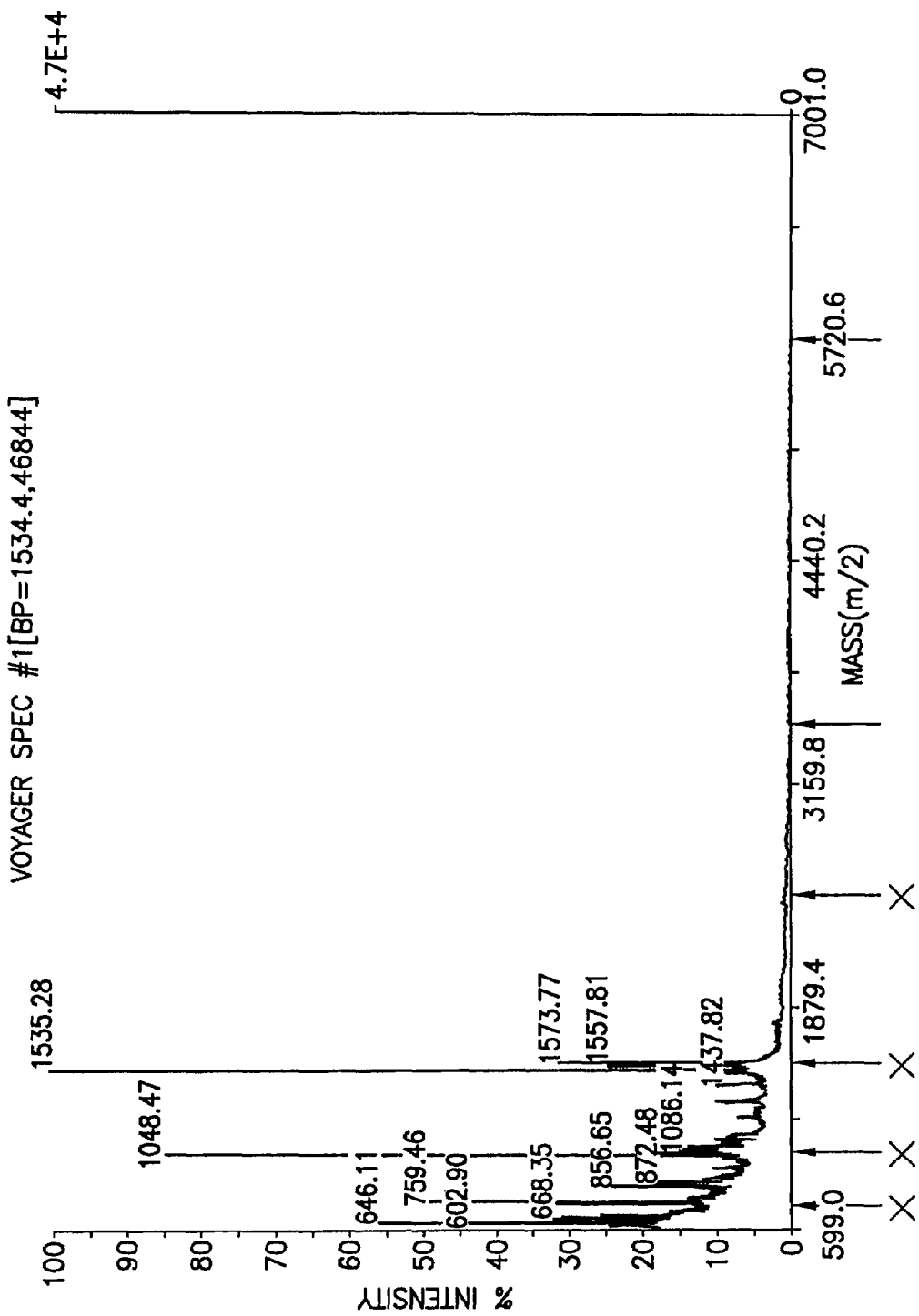
FIGS. 9-15 show various mass spectra.
Figure 9B:
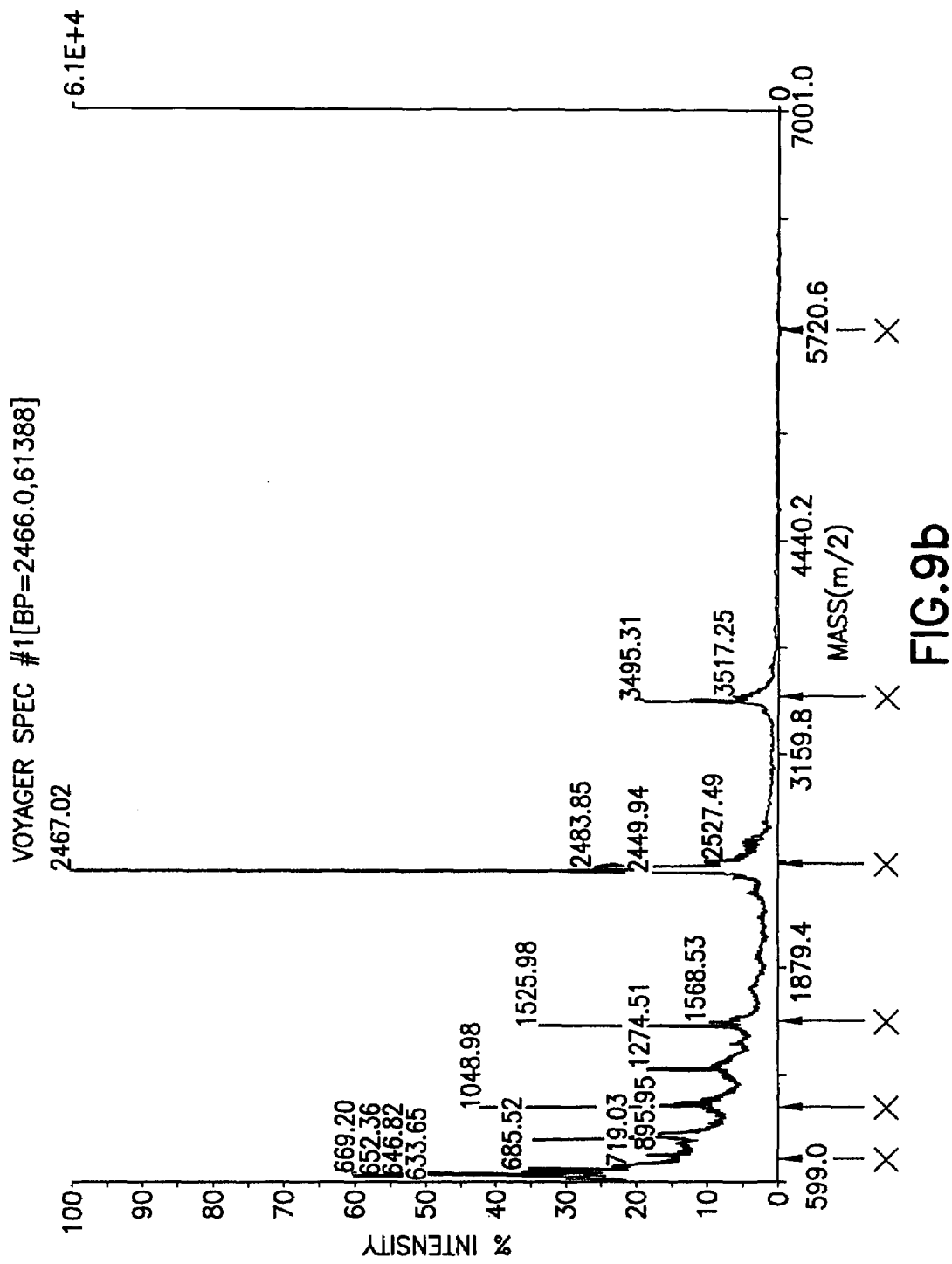
Figure 10A:
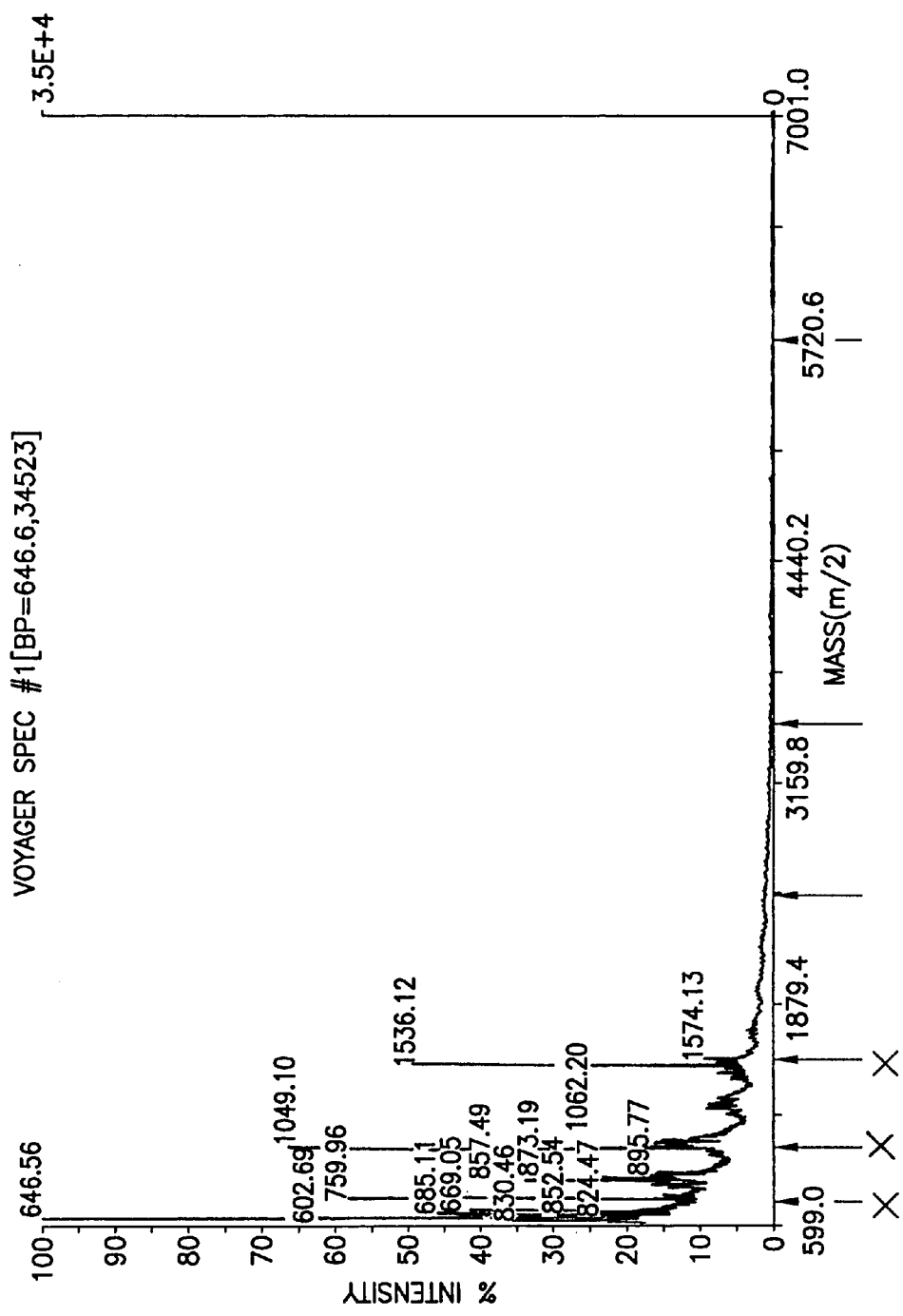
Figure 10B:
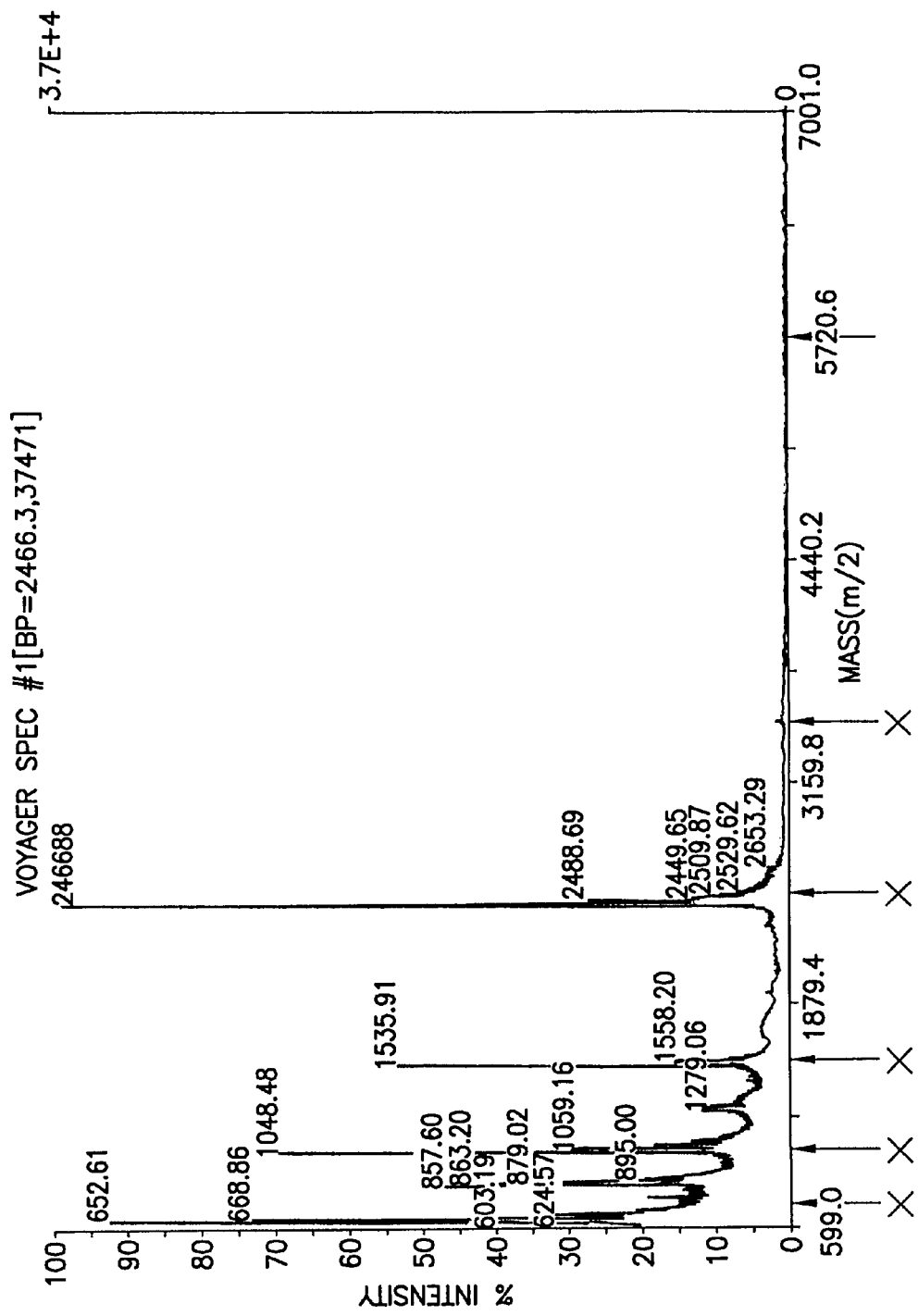
Figure 11A:
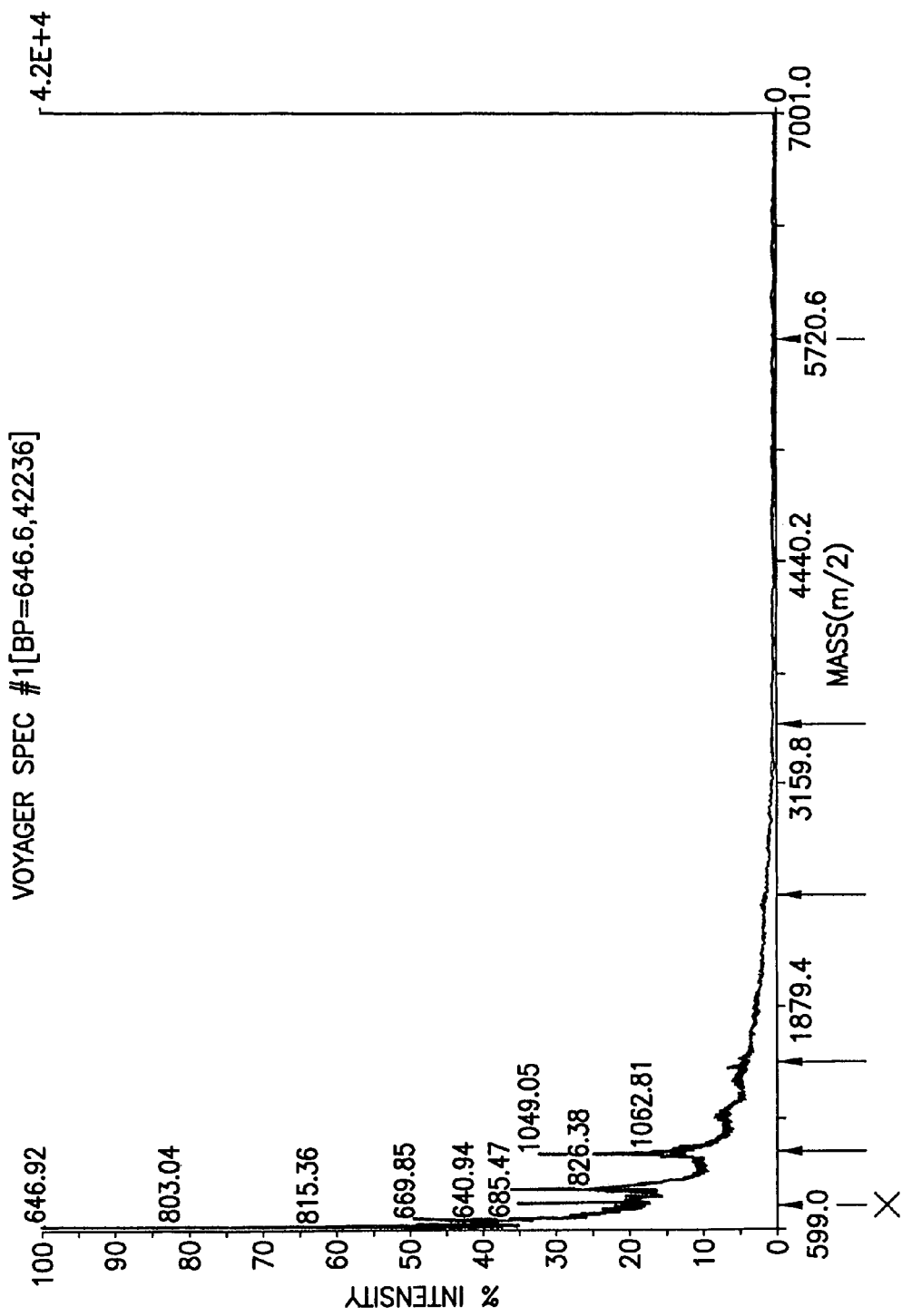
Figure 11B:
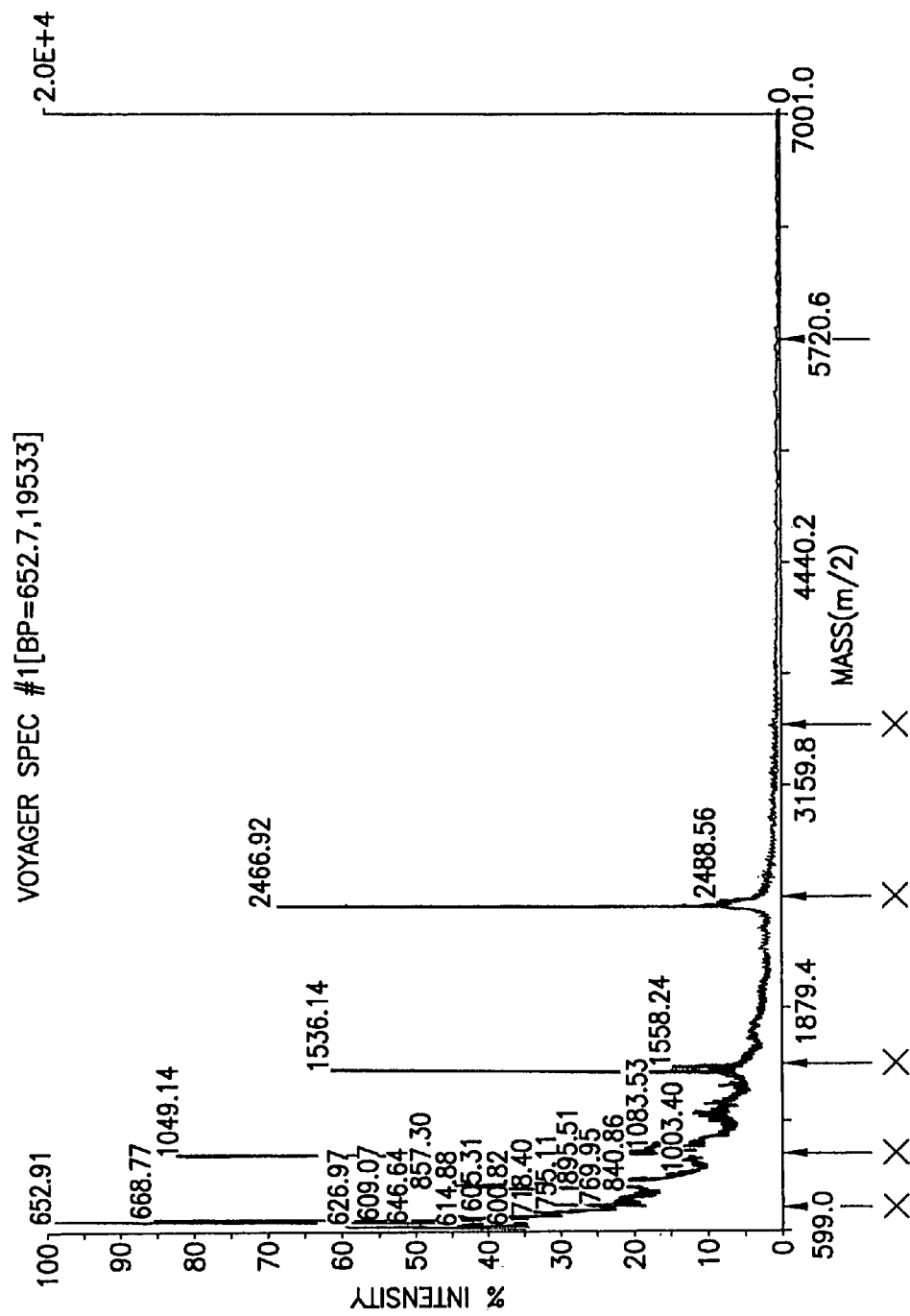
Figure 12A:
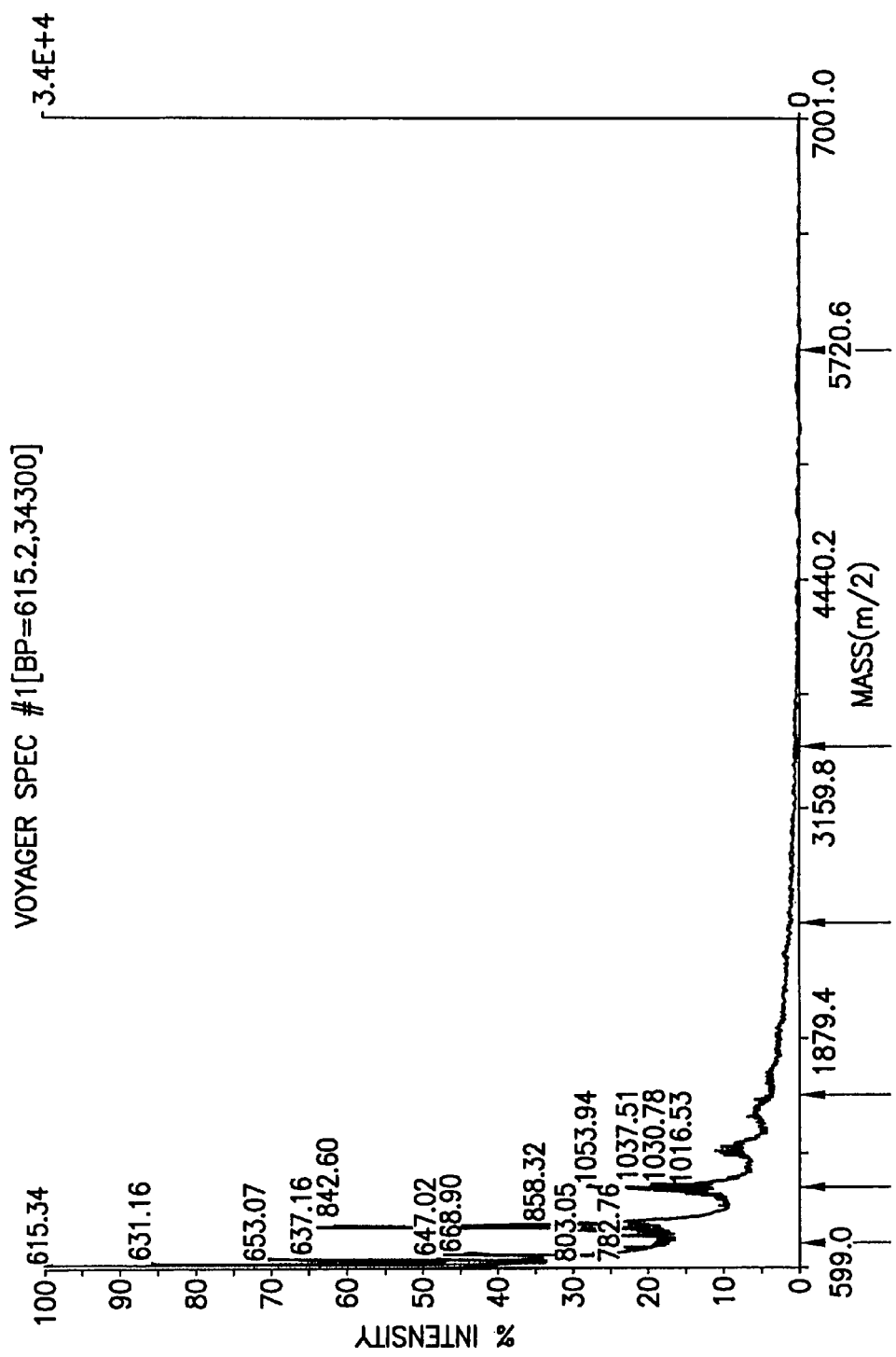
Figure 12B:
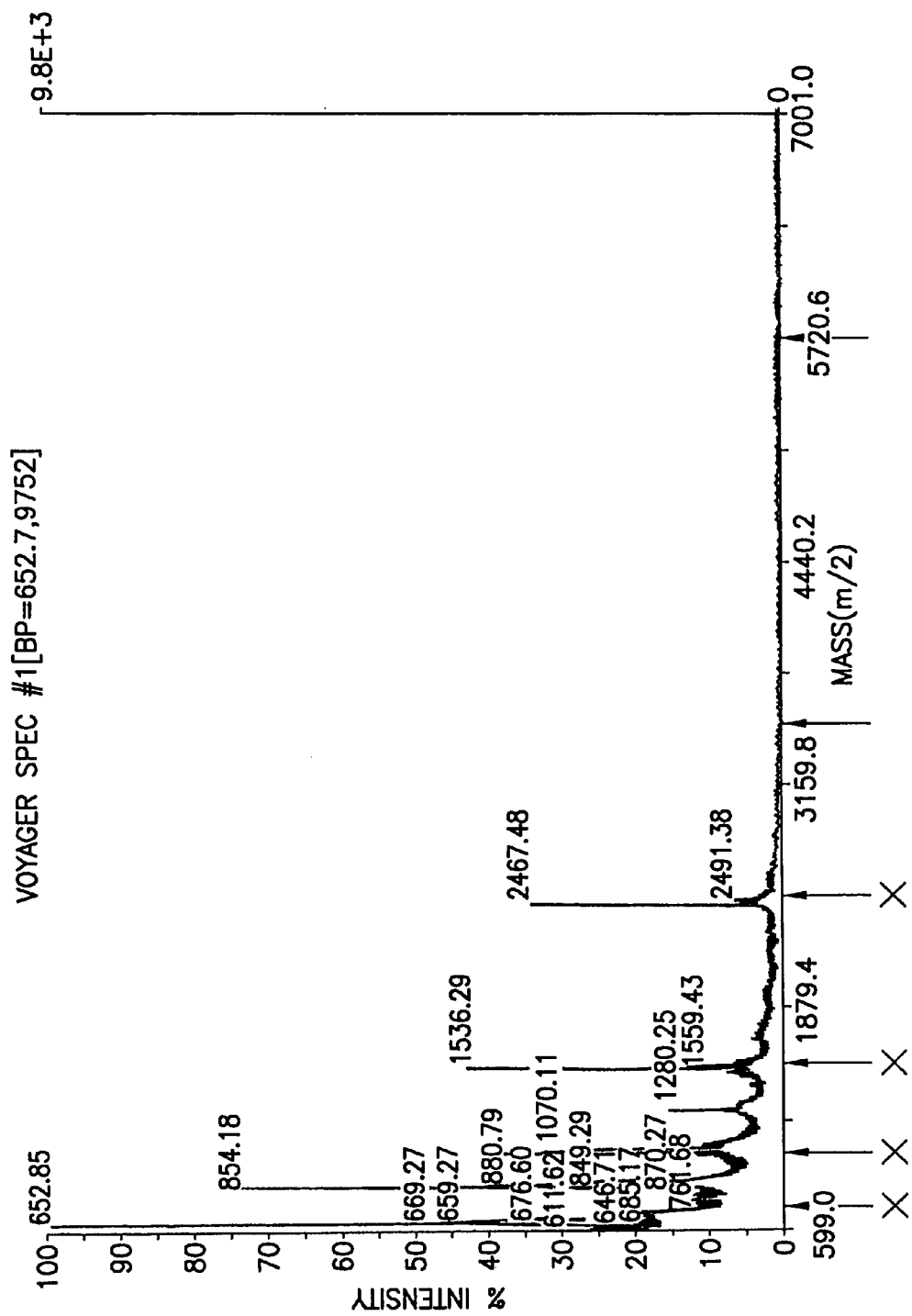

With the process of the subject invention, purer samples can be obtained than in the prior art which result in better analysis. FIGS. 9-12 show a comparison between the same sample solutions having been processed using pipette tips with C18 media versus the method described above in conjunction with FIG. 8. FIGS. 9(*a*), 10(*a*), 11(*a*) and 12(*a*) are mass spectra obtained from sample solutions prepared by pipette tips with C18 media, while FIGS. 9(*b*), 10(*b*), 11(*b*) and 12(*b*) were prepared using the method associated with FIG. 8 of the subject application. The mass spectra of FIG. 9 were obtained for a sample solution (50μL) containing 100 nM peptide standards; the mass spectra of FIG. 10 were obtained for a sample solution (50 μL) containing 50 nM peptide standards; the mass spectra of FIG. 11 were obtained for a sample solution (50μL) containing 20 nM peptide standards; and the mass spectra of FIG. 12 were obtained for a sample solution (50μL) containing 10 nM peptide standards. The arrows below the x-axis in each of the mass spectra indicate the expected peak positions of the six standard peptides (Human bradykinin fragment 1-7, M.W.=757.4; Human angiotensin II, M.W.=1046.5; Synthetic peptide $P_{14}R$, M.W.=1533.9; Human ACTH fragment 18-39, M.W.=2465.2; Bovine insulin oxidized B chain, M.W.=3494.7; Bovine insulin, M.W.=5734.5), while a "X" indicates that a matching peak is found in the spectrum. It must be noted that some of the peaks in the low molecular weight region are contributed by the MALDI matrix α-cyano-4-hydroxy cinnamic acid (CHCA). As will be noted, more matching peaks were detected by the subject invention than with the conventional tips with C18 media.

Figure 13A:
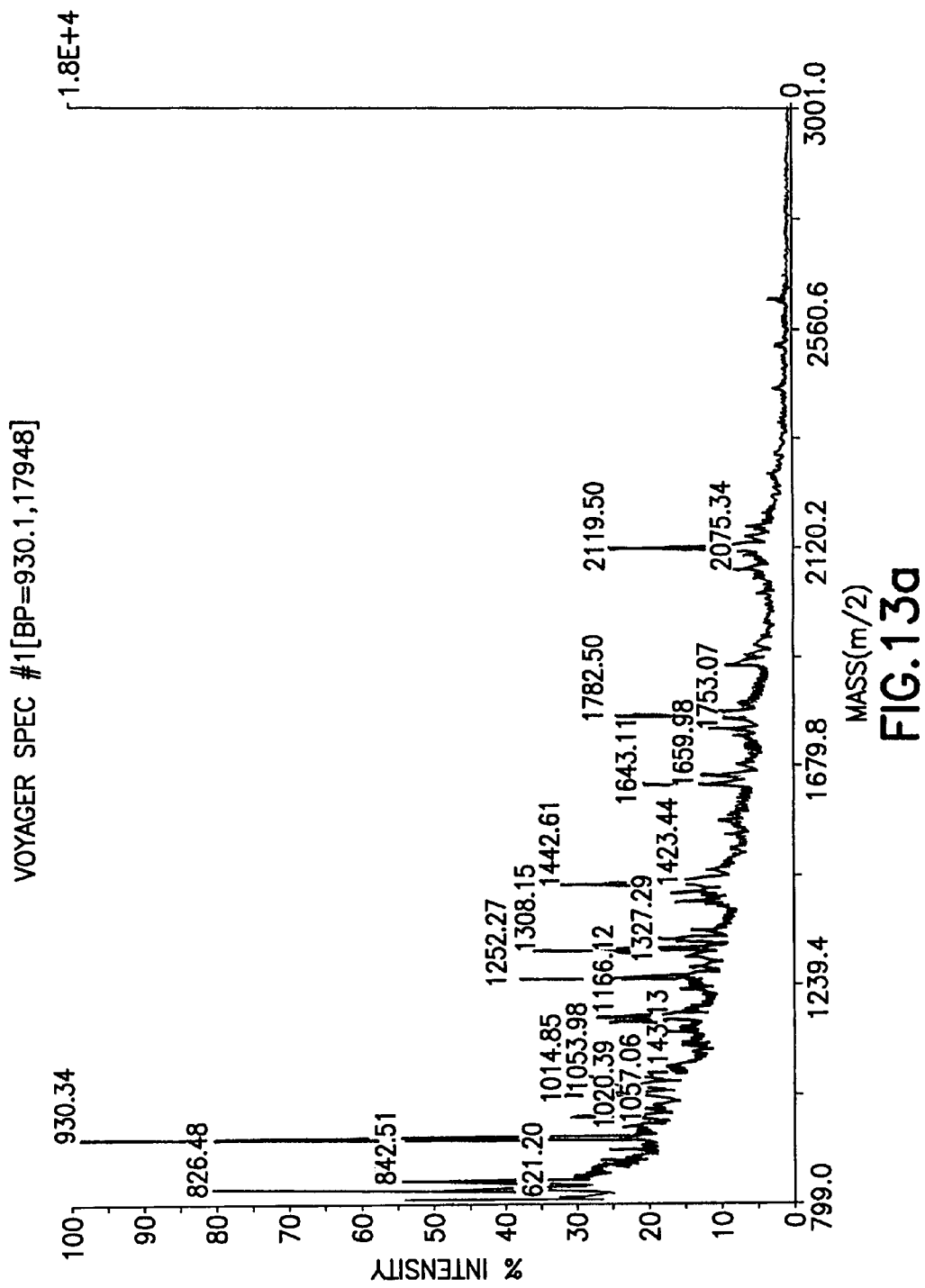
Figure 13B:
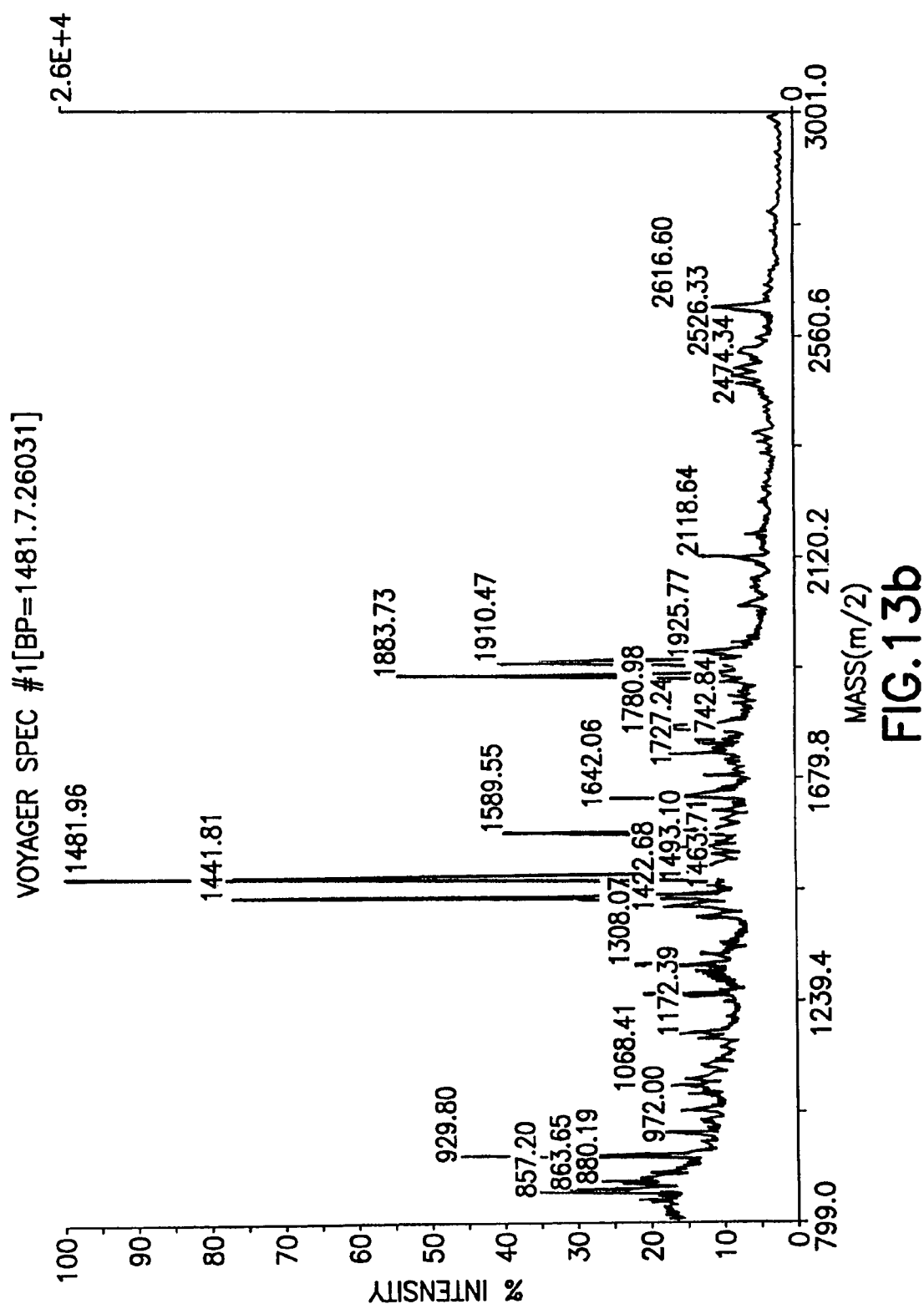
Figure 14A:
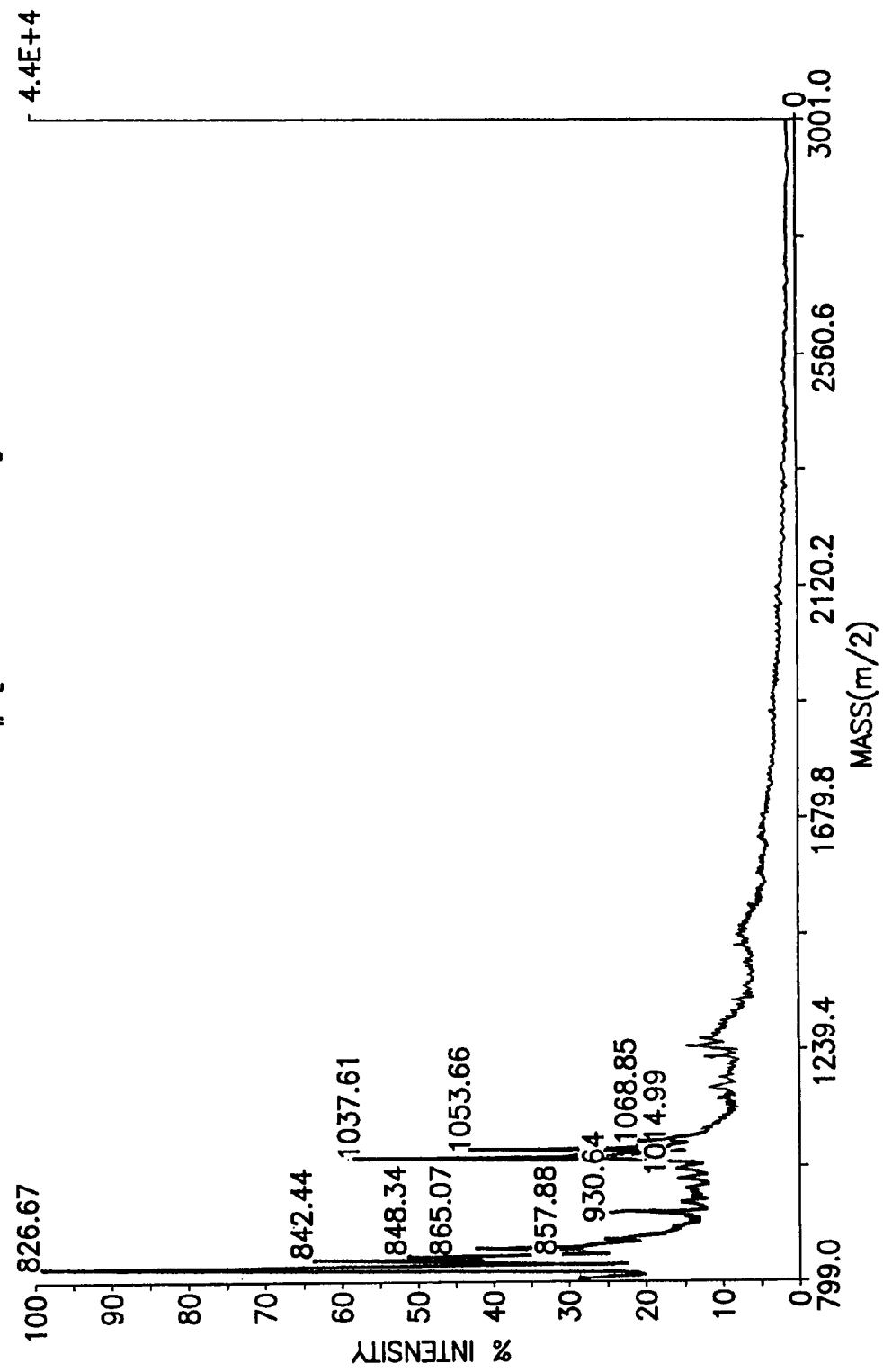
Figure 14B:
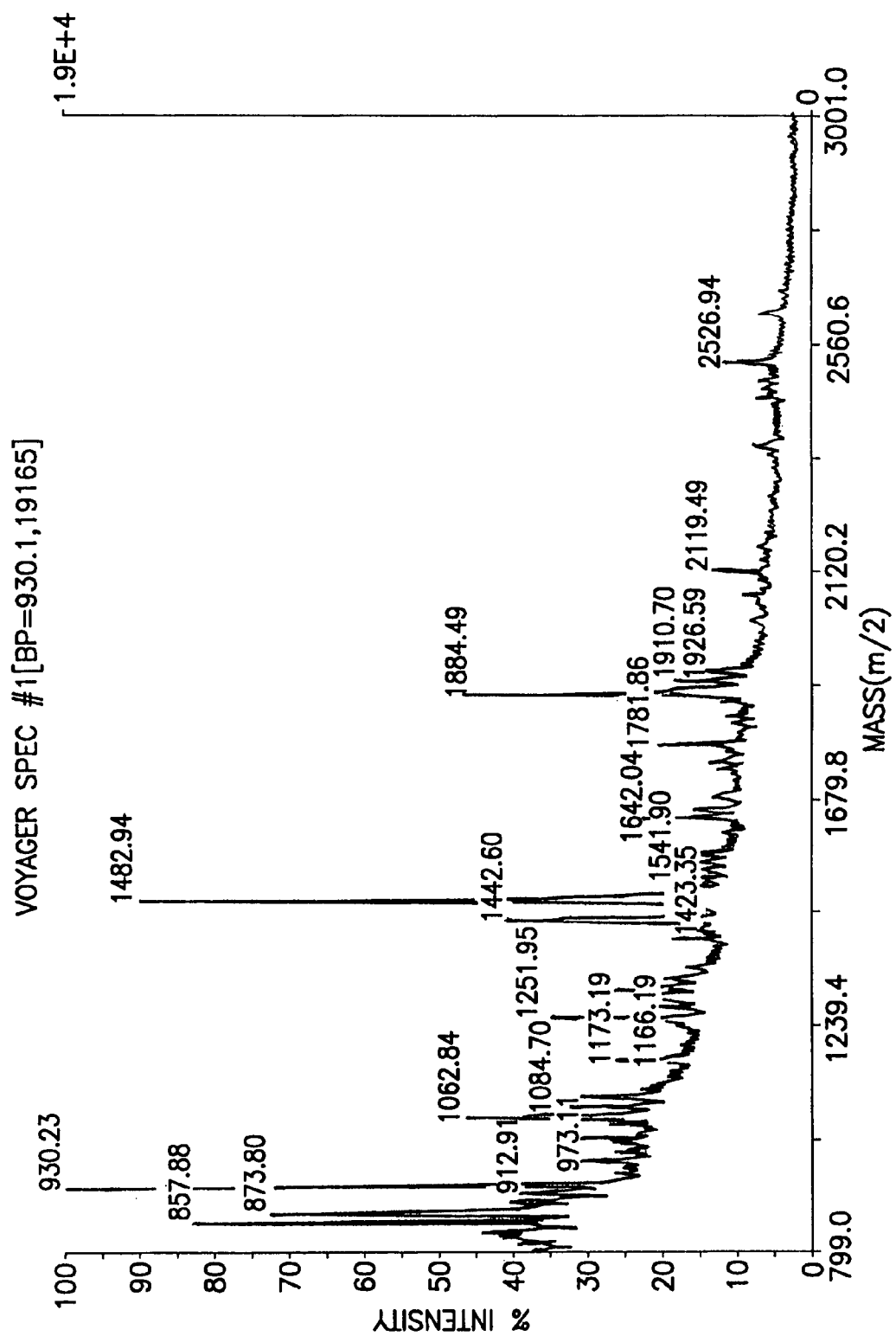
Figure 15B:
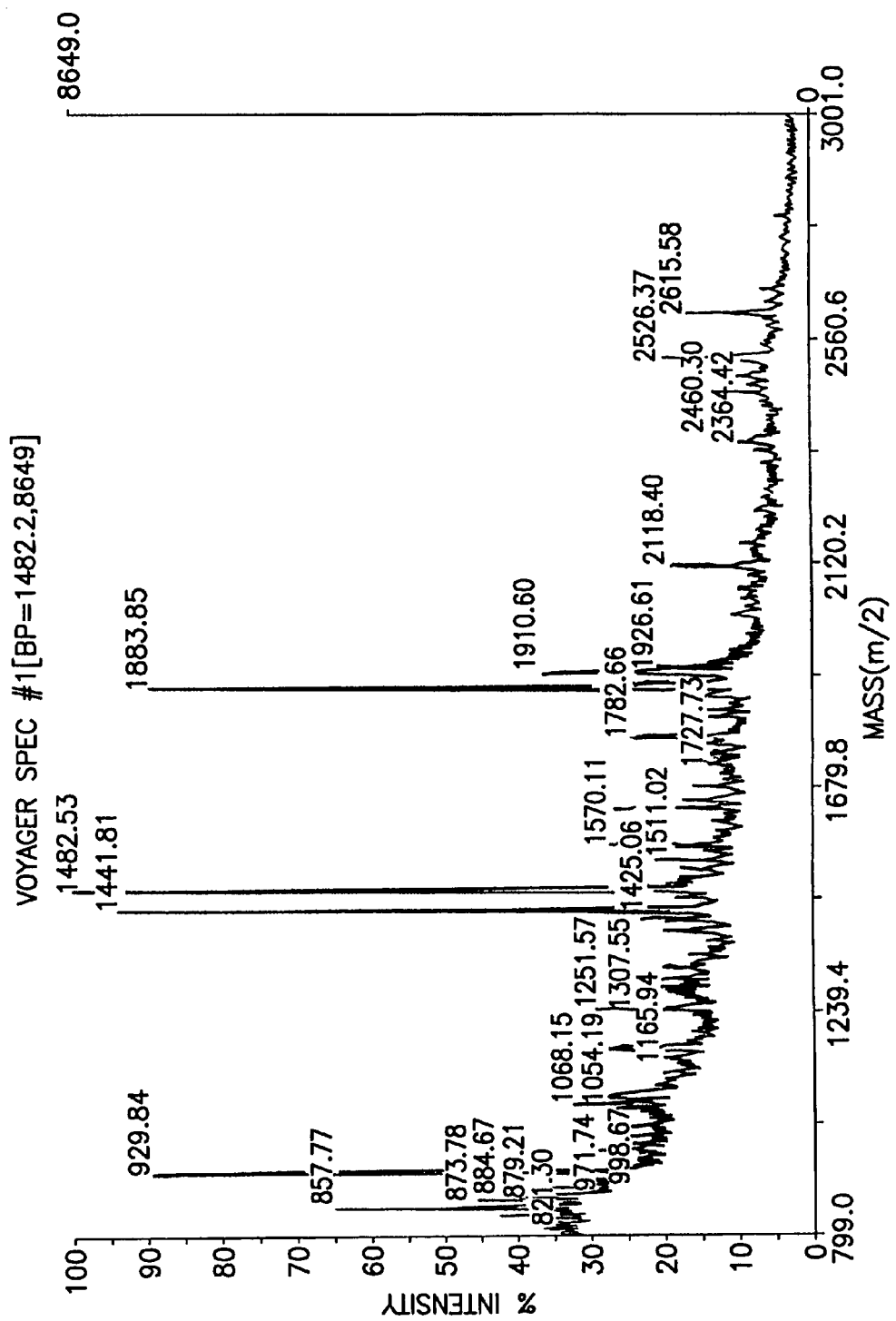

FIG. 13-15 show a similar comparison, where FIG. 13(a), 14(a) and 15(a) were obtained by using pipette tips with C18 media, while FIGS. 13(b), 14(b) and 15(b) were obtained using the subject invention. The mass spectra in FIG. 13 were obtained for a sample solution (50 μL) containing 50 nM Bovine Serum Albumin (BSA) tryptic digest, the mass spectra in FIG. 14 were obtained for a sample solution (50 μL) containing 20 nM BSA tryptic digest, and the mass spectra in FIG. 15 were obtained for a sample solution (50 μL) containing 10 nM BSA tryptic digest. As can be seen from FIGS. 13-15, more peptide peaks from the BSA tryptic digest were resolved by the subject invention than with the conventional tips with C18 media, indicating a better recovery of peptides from the purification process.

Various changes and modifications can be made in the present invention. It is intended that all such changes and modifications come within the scope of the invention as set forth in the following claims.

What is claimed is:

1. A process for purifying a biological or chemical sample, said process comprising:
    providing an article having a well with a surface which is at least partially hydrophobic, said well having an open end and a closed end;
    depositing a liquid sample in said well, said liquid sample being a solution including liquid and first and second classes of solutes;
    evaporating said liquid from said liquid sample such that said first and second classes of solutes come out from solution from said liquid sample, said first class of solutes in said sample tightly binding to said surface, and said second class of solutes in said sample not tightly binding to said surface;
    depositing a first buffer in said well, said first buffer disassociating said second class of solutes from said surface;
    removing said first buffer and said disassociated second class of solutes from said well;
    depositing a second buffer in said well after removing said first buffer, said second buffer disassociating said first class of solutes from said surface.

2. A process as in claim 1, wherein said article is a multi-well plate.

3. A process as in claim 1, wherein said article is a column.

4. A process as in claim 1, wherein said article is a pipette.

5. A process as in claim 1, wherein said article includes a target support plate having spaced-apart top and bottom surfaces, at least one column extending between, and through, said top and bottom surfaces, and a target device secured to said target support plate, said target device having at least one collection site, said column registering with said collection site, said column and said collection site collectively defining said well.

6. A process as in claim 5, wherein said target device is releasably secured to said target support plate.

7. A process as in claim 5, wherein at least the bottom surface of said target support plate is formed of an elastomeric material releasably adhered to said target device.

8. A process as in claim 7, wherein said elastomeric material includes a silicon polymer.

9. A process as in claim 7, wherein said elastomeric material includes poly(dimethyl)siloxane.

10. A process as in claim 7, wherein said target support plate is wholly formed of said elastomeric material.

11. A process as in claim 5, wherein said target device is a mass spectrometry plate.

12. A process as in claim 1, wherein said article is at least partially formed of an elastomeric material.

13. A process as in claim 12, wherein said elastomeric material includes a silicon polymer.

14. A process as in claim 12, wherein said elastomeric material includes poly(dimethyl)siloxane.

15. A process as in claim 12, wherein said article is wholly formed of said elastomeric material.

16. A process as in claim 1, wherein said liquid sample includes tryptic digest products.

17. A process as in claim 1, wherein said first class of solutes includes peptides.

18. A process as in claim 1, wherein said first class of solutes includes proteins.

19. A process as in claim 1, wherein said second class of solutes includes salts.

20. A process as in claim 1, wherein said second class of solutes includes small molecule contaminants.

21. A process as in claim 1, wherein said first buffer includes water.

22. A process as in claim 1, wherein said second buffer includes an organic solvent.

23. A process as in claim 1, wherein said second buffer includes an energy absorbing matrix.

24. A process as in claim 1, wherein said surface is a coating including one or more selected from the group consisting of alkyl silanes and hydrophobic polymers.

25. A process as in claim 1, further comprising the step of evaporating said second buffer, leaving said first class of solutes in said well.

* * * * *